United States Patent
Carucci et al.

(10) Patent No.: US 11,304,910 B2
(45) Date of Patent: Apr. 19, 2022

(54) SOFT GELATIN CAPSULES WITH PH-INDEPENDENT RELEASE

(71) Applicant: Altergon S.A., Lugano (CH)

(72) Inventors: Simone Carucci, Lugano (CH); Maurizio Marchiorri, Lugano (CH); Marco Pontiggia, Lugano (CH); Tiziano Fossati, Lugano (CH)

(73) Assignee: Altergon S.A., Lugano (CH)

( * ) Notice: Subject to any disclaimer, the term of this patent is extended or adjusted under 35 U.S.C. 154(b) by 156 days.

(21) Appl. No.: 15/781,708

(22) PCT Filed: Nov. 25, 2016

(86) PCT No.: PCT/EP2016/078913
§ 371 (c)(1),
(2) Date: Jun. 6, 2018

(87) PCT Pub. No.: WO2017/097612
PCT Pub. Date: Jun. 15, 2017

(65) Prior Publication Data
US 2018/0353432 A1    Dec. 13, 2018

(30) Foreign Application Priority Data
Dec. 9, 2015   (IT) .................. 102015000081410

(51) Int. Cl.
| A61K 9/48 | (2006.01) |
| A61K 47/10 | (2017.01) |
| A61K 31/198 | (2006.01) |
| A61K 45/06 | (2006.01) |
| A61K 47/02 | (2006.01) |
| A61K 47/26 | (2006.01) |
| A61K 47/40 | (2006.01) |

(52) U.S. Cl.
CPC .......... *A61K 9/4825* (2013.01); *A61K 9/4866* (2013.01); *A61K 31/198* (2013.01); *A61K 45/06* (2013.01); *A61K 47/02* (2013.01); *A61K 47/10* (2013.01); *A61K 47/26* (2013.01); *A61K 47/40* (2013.01)

(58) Field of Classification Search
CPC ...... A61K 9/4825; A61K 9/0095; A61K 9/14; A61K 9/4866; A23L 33/125; A23L 33/15; A23L 33/16; A23L 33/17; A61P 13/12
See application file for complete search history.

(56) References Cited

U.S. PATENT DOCUMENTS

| 4,795,642 A * | 1/1989 | Cohen .................. A61K 9/4858 264/4.3 |
| 5,102,666 A * | 4/1992 | Acharya ................ A61K 8/733 424/422 |
| 8,540,980 B2 * | 9/2013 | London ................ A61K 9/2063 424/93.45 |
| 2003/0050344 A1 * | 3/2003 | Garavani ............... A61K 9/485 514/567 |
| 2004/0138098 A1 * | 7/2004 | Fein ...................... A61K 9/0056 514/10.9 |
| 2008/0107779 A1 * | 5/2008 | Kelvin .................. A21C 15/025 426/95 |
| 2009/0130251 A1 * | 5/2009 | Perry .................... A23G 3/0085 426/5 |
| 2009/0269405 A1 * | 10/2009 | Windsor ............... A61K 9/5052 424/484 |

FOREIGN PATENT DOCUMENTS

| EP | 0243930 A1 | 11/1987 |
| EP | 1315479 A1 | 6/2003 |
| WO | 1984003416 A1 | 9/1984 |
| WO | 1995011668 A1 | 5/1995 |
| WO | 1999022768 A1 | 5/1999 |
| WO | WO 2007/075475 | * 7/2007 |

OTHER PUBLICATIONS

Ishmael J .et al., "Indomethacin sustained release from alginate-gelatin or pectin-gelatin coacervates", International Journal of Pharmaceutics 126 (1995) 161-168.
Search Report and Written Opinion of PCT/EP2016/078913 dated Feb. 27, 2017.

* cited by examiner

*Primary Examiner* — Andrew S Rosenthal
*Assistant Examiner* — Lyndsey M Beckhardt
(74) *Attorney, Agent, or Firm* — Silvia Salvadori, P.C.; Silvia Salvadori

(57) ABSTRACT

Disclosed are soft gelatin capsules comprising a gelatin shell, a plasticiser, water, and optionally a calcium salt and a filling containing a dispersed or solubilised medicament comprising gelatin with gelling power, hydrolysed gelatin, glycerol, water, pectin and gellan gum. The formulations according to the invention allow gradual release of the active ingredient, regardless of pH.

9 Claims, 4 Drawing Sheets

SOFT GELATIN CAPSULES WITH PH-INDEPENDENT RELEASE

This application is a U.S. national stage of PCT/EP2016/078913 filed on 25 Nov. 2016, which claims priority to and the benefit of Italian Application No. 102015000081410 filed on 9 Dec. 2015, the contents of which are incorporated herein by reference in their entireties.

The present invention relates to a novel formulation for soft gelatin capsules that allows the modulation of pH-independent release of both poorly water-soluble and water-soluble active ingredients or complexes thereof designed to increase the solubility of active ingredients that are poorly soluble or insoluble in water.

STATE OF THE ART

The pharmaceutical form consisting of a soft gelatin capsule is used for the administration (mainly oral) of non-crystalline, poorly water-soluble active ingredients. For example, preparations of progesterone and vitamin complexes in the form of soft gelatin capsules are present on the market.

Soft gelatin capsules consist of a shell containing plasticised gelatin that encloses a filling material, usually consisting of a liquid or semi-liquid lipophilic active ingredient, a solution of a lipophilic active ingredient or a paste, which have characteristics such that the shell is not dissolved.

It is known from EP1315479 that hard capsules containing pectin, gellan gum and calcium chloride in a gelatin shell with gelling power do not release the active ingredient at acid pH values (e.g. pH 1.2), whereas at pH values close to neutrality (e.g. pH 6.8) they release the entire contents of the capsule in a few minutes. EP1315479 therefore describes gastroprotected capsules, and does not teach that the combination of gelatin with gelling power, pectin, gellan gum and calcium chloride can lead to pH-independent, modulatable, slow release.

DESCRIPTION OF THE INVENTION

Figure 1:
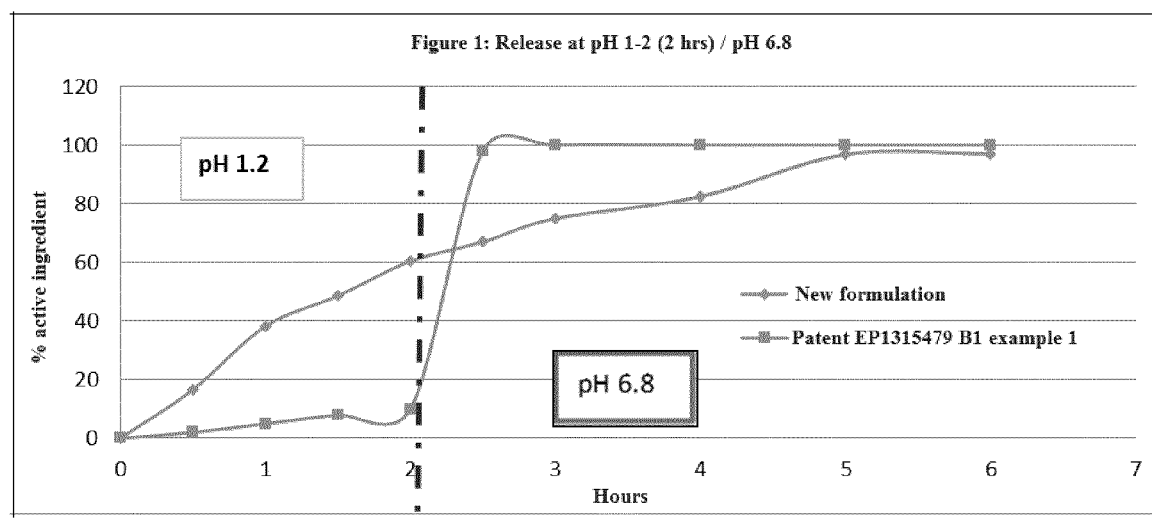
FIG. 1 is a comparison of the formulation of example 1 with example 1 of patent EP1315479.

It has now surprisingly been found, contrary to the teachings derivable from the prior art, that according to a first aspect of the invention, new soft capsule formulations can be obtained that allow the release of the active ingredients to be modulated and prolonged, by dispersing a solution or suspension of the medicament in a hydrophilic filling consisting of gelatin with gelling power, hydrolysed gelatin, glycerol, water, pectin and gellan gum. The filling thus formulated is enclosed in a shell made of gelatin, anhydrous glycerol, water, and optionally calcium chloride.

The object of the invention is therefore pharmaceutical formulations in the form of soft gelatin capsules comprising a gelatin shell, a plasticiser such as anhydrous glycerol or other polyols, water and optionally a calcium salt, which said shell contains a medicament dispersed or solubilised in a hydrophilic filling comprising gelatin with gelling power, hydrolysed gelatin, glycerol, water, pectin and gellan gum.

The formulations according to the invention are advantageously suitable for both poorly water-soluble active ingredients and water-soluble active ingredients, and also for active ingredients which poorly soluble or insoluble, complexed to increase their solubility. For example, the medicament can be in a form complexed with cyclodextrin.

Examples of active ingredients usable according to the invention include non-steroidal anti-inflammatory drugs, thyroid hormones (levothyroxine, liothyronine), statins, bronchodilators, antihistamines, steroids and derivatives thereof, narcotic analgesics, antibacterials/antivirals, vitamins, oils of various kinds (fish oil, crustacean oil, plant oils and essential oils), glycosaminoglycans, antimycotics, proton pump inhibitors, fertility hormones (FSH, HCG, HMG, LH), corticosteroids, erectile dysfunction medicaments and anticoagulants.

Examples of soluble medicaments usable according to the invention include metformin hydrochloride, propranolol hydrochloride, ranitidine hydrochloride and diltiazem hydrochloride, while non-limiting examples of averagely water-soluble medicaments (from 1 to 100 mg/ml), usable according to the invention, include paracetamol, paroxetine, duloxetine, tamsulosin, atomoxetine, fluoxetine and salts thereof.

The formulations of the invention are in any event suitable for any compound designed for oral administration.

The medicament can be introduced into the filling "as is", in solution, or in ethanol suspension.

"Gelatin with gelling power" herein means a gelatin with a Bloom value of 60 to 360, preferably 60 to 120.

"Hydrolysed gelatin" herein means a gelatin which has undergone enzymatic digestion. Hydrolysed gelatin is available on the market from various sources, and is rich in glycine, proline, hydroxyproline, lysine and hydroxylysine.

Gellan gum is an unbranched polymer of bacterial origin formed by the repeating tetrasaccharide unit glucose-rhamnose-glucose-glucuronic acid. It is used as a food additive, cosmetic additive and pharmaceutical additive as emulsifier, thickener and stabiliser, and is available from various commercial sources.

Pectin is a heteropolysaccharide comprising units of galacturonic acid linked by α(1-4) bonds whose carboxyl groups are partly in the form of methyl esters. The degree of esterification of pectin is defined as the ratio between the esterified groups and the total carboxyl groups.

The shell of the capsule preferably contains 20 to 45% gelatin with a Bloom value between 110 and 300, 15 to 30% plasticiser, 30 to 40% water and optionally 0.5 to 5%, preferably 1 to 2%, calcium salt, preferably calcium chloride.

Said plasticiser can preferably be selected from polyhydroxy alcohols, preferably selected from glycerol, sorbitol, sorbitol/sorbitan mixtures, 1,2 propylene glycol, macrogol 200-600 and mixtures thereof.

The percentages are expressed by weight on the total shell weight.

The capsule filling preferably contains 1 to 5% gelatin with a Bloom value ranging between 60 and 150, 10 to 30% hydrolysed gelatin, 10 to 30% of 85% glycerol, 1 to 5% pectin, up to 5% gellan gum, 20 to 60% water, and 0.1 to 10% alcohol. The percentages are expressed by weight on the total shell weight. The percentage of active ingredient will obviously depend on the unit dose chosen.

The invention allows the release of the active ingredient in a pH-independent way; the release can be modulated by increasing or reducing the quantity of pectin and its degree of esterification and modifying the quantity of gellan gum in the presence of hydrolysed gelatin. The release can be further prolonged by adding calcium chloride to the shell. As will be clear from the examples set out below, more gradual release is obtained by using pectin and gellan gum in percentages close to the highest values of the intervals specified above.

The invention is illustrated in greater detail in the examples below.

EXAMPLE 1

Effect of CaCl$_2$ in Shell

|  | without CaCl$_2$ | with CaCl$_2$ |
|---|---|---|
| Filling excipients | mg/cps | mg/cps |
| Liothyronine sodium T3 | 0.025 | 0.025 |
| Hydrolysed gelatin | 17.5 | 17.5 |
| 80 bloom pigskin gelatin | 2.5 | 2.5 |
| 85% glycerol | 15 | 15 |
| 96% ethanol | 2.5 | 2.5 |
| Pectin CU 401-USP | 3.482 | 3.482 |
| Gellan gum | 0.0893 | 0.0893 |
| Purified water | 58.9037 | 58.9037 |
| Total Filling | 100 | 100 |
| Shell excipients | mg/cps | mg/cps |
| 150 bloom gelatin | 97.5 | 97.5 |
| Anhydrous glycerol | 57.5 | 57.5 |
| Calcium chloride | — | 5 |
| Purified water | 95 | 90 |
| Total wet shell | 250 | 250 |
| Total dry capsule | 255 | 260 |

FIG. 1 compares the formulation of example 1 with example 1 of patent EP1315479.

Figure 2:
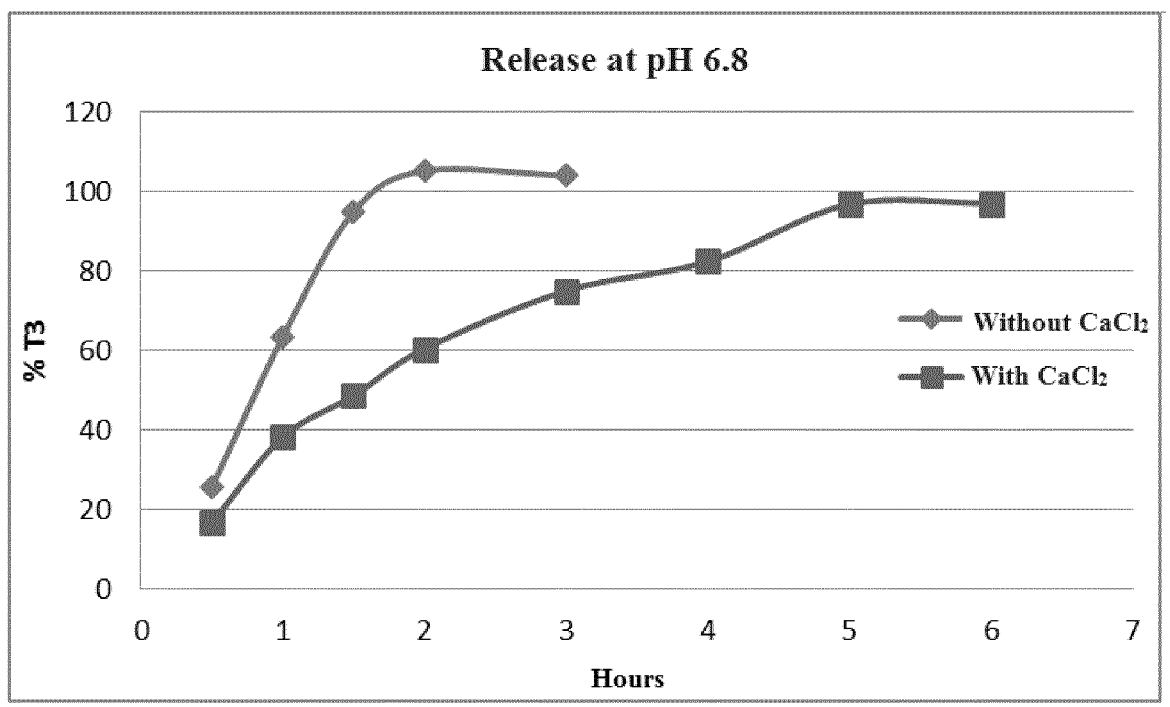
FIG. 2 shows the release profile in the shell in the presence or absence of $CaCl_2$ at pH 6.8.
Figure 3:
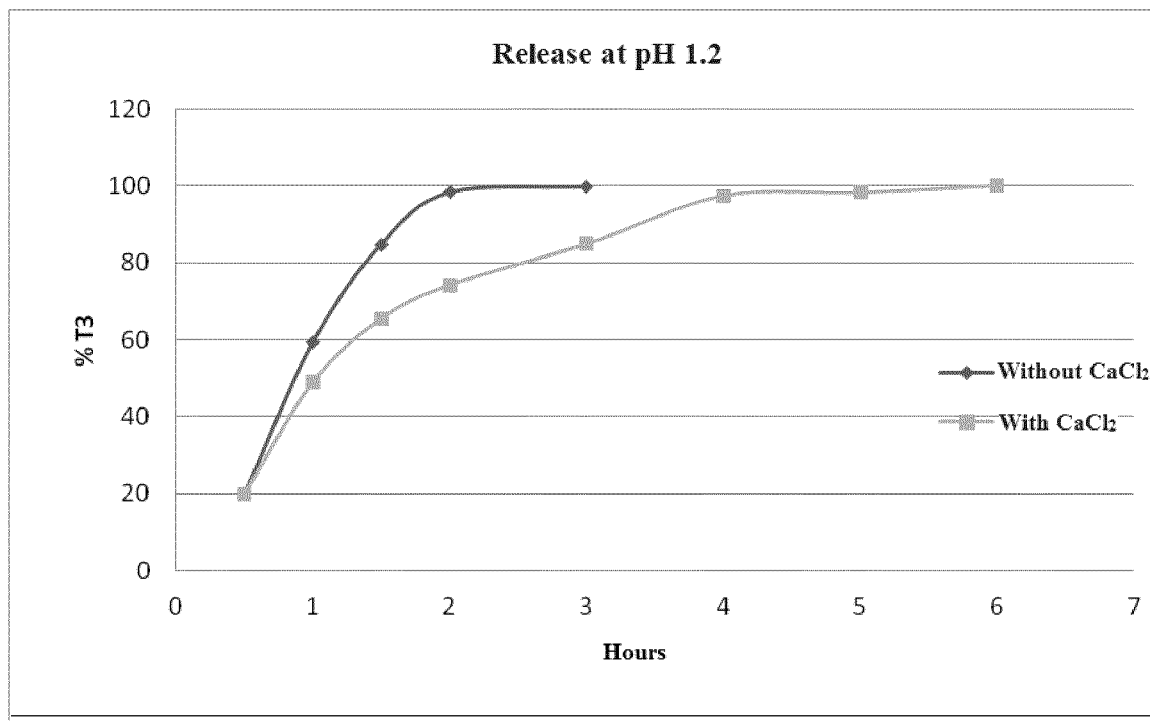
FIG. 3 shows the release profile in the shell in the presence or absence of $CaCl_2$ at pH 1.2.

FIGS. 2 and 3 show the release profiles in the shell, in the presence or absence of CaCl$_2$, at pH 6.8 and 1.2 respectively.

EXAMPLE 2

Effect of Pectin and Gellan Gum on Release

| Filling | example 2 form 1 mg/cps | example 2 form 2 mg/cps | example 2 form 3 mg/cps |
|---|---|---|---|
| Liothyronine sodium | 0.025 | 0.025 | 0.025 |
| Hydrolysed gelatin | 17.500 | 23.335 | 28.000 |
| 80 bloom gelatin | 2.500 | 3.334 | 4.000 |
| 85% glycerol | 15.000 | 20.001 | 24.000 |
| 96% ethanol | 2.500 | 3.334 | 4.000 |
| Pectin CU 401-USP | 3.482 | 2.321 | 1.393 |
| Gellan gum | 0.089 | 0.060 | 0.036 |
| Purified water | 58.904 | 47.592 | 38.546 |

| Filling | example 2 form 1 mg/cps | example 2 form 2 mg/cps | example 2 form 3 mg/cps |
|---|---|---|---|
| Shell |  |  |  |
| 150 bloom gelatin | 97.50 | 97.50 | 97.50 |
| Anhydrous glycerol | 57.50 | 57.50 | 57.50 |
| Calcium chloride dihydrate | 5.00 | 5.00 | 5.00 |
| Purified water | 90.00 | 90.00 | 90.00 |

Figure 4:
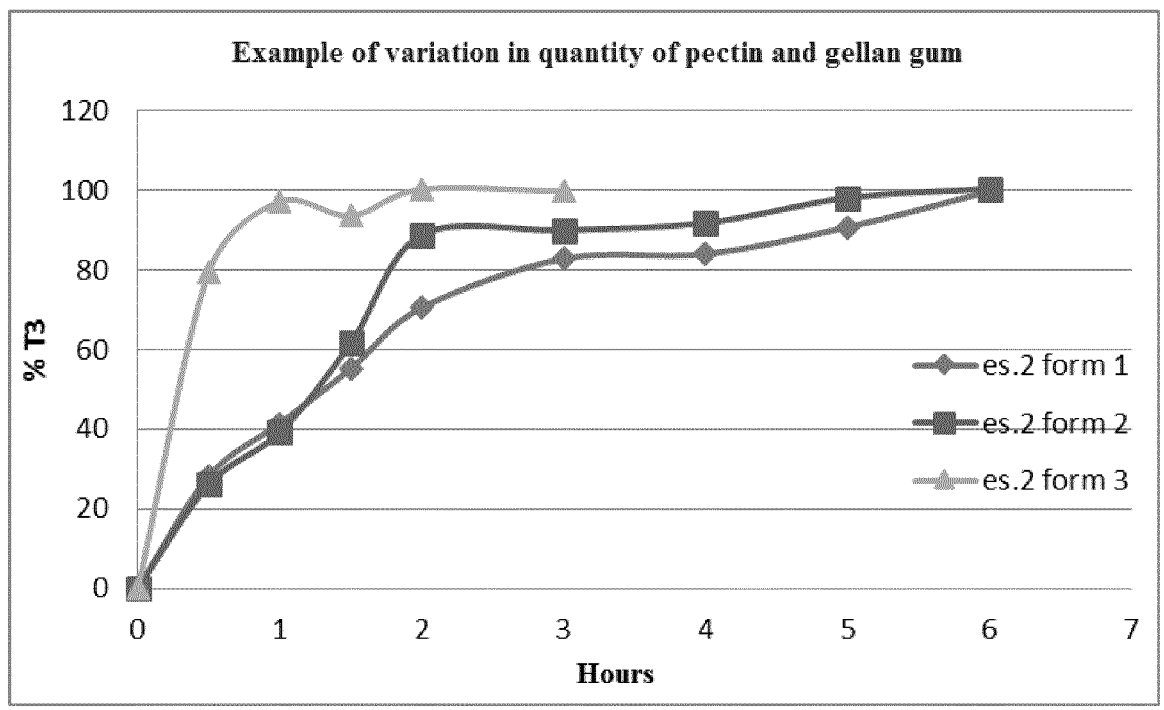
FIG. 4 shows the results of the release properties in function of the variation in quantity of pectin and gellan gum in different formulations.

A comparison of the release properties demonstrates that the formulation with the highest pectin and gellan gum content leads to slower release. The results are shown in FIG. 4.

The invention claimed is:

1. A soft gelatin capsule, wherein the capsule comprises a shell containing gelatin, a plasticizer, water and a calcium salt and
a filling,
wherein the filling contains a medicament dispersed or solubilised in a hydrophilic filling comprising from 1 to 5% of gelatin having a Bloom value ranging from 60 to 150 in percentages, said gelatin having gelling power, from 10 to 30% of hydrolyzed gelatin, from 10 to 30% of 85% glycerol, from 20 to 60% water, from 10 to 30% of pectin, up to 5% of gellan gum and from 0.1 to 10% of alcohol, the percentages being expressed by weight, on the total filling weight, wherein said soft gelatin capsule allows, in vitro, releasing of said medicament in a sustained pH-independent manner, said releasing beginning at the release time of said medicament and continuing for up to 360 minutes.

2. A capsule according to claim 1 wherein the medicament can be dispersed or solubilised by means of ethanol or other hydrophilic or lipophilic solvents, and/or complexed with cyclodextrin.

3. A capsule according to claim 1 wherein the shell contains calcium chloride.

4. A capsule according to claim 1, wherein the medicament is selected from non-steroidal anti-inflammatory drugs, thyroid hormones, statins, bronchodilators, antihistamines, steroids, narcotic analgesics, antibacterials/antivirals, vitamins, oils of various kinds, glycosaminoglycans, antimycotics, proton pump inhibitors, fertility hormones, corticosteroids, erectile dysfunction medicaments, and anticoagulants.

5. A capsule according to claim 1 wherein the she contains from 20 to 45% of gelatin having a Bloom value ranging from 110 to 300, plasticizer from 15 to 30%, water from 30 to 40% and a calcium salt, the percentages being on the total shell weight.

6. A capsule according to claim 5 wherein the calcium salt is calcium chloride.

7. A capsule according to claim 6 wherein calcium chloride is present in percentages by weight ranging from 0.5 to 5% on the total shell weight.

8. A capsule according to claim 1, wherein the plasticizer is selected from anhydrous glycerol, sorbitol, sorbitol/sorbitan mixtures, 1,2 propylene glycol, macrogol 200-600 and mixtures thereof.

9. A capsule according to claim 8 wherein the plasticizer is anhydrous glycerol.

* * * * *

UNITED STATES PATENT AND TRADEMARK OFFICE
CERTIFICATE OF CORRECTION

PATENT NO. : 11,304,910 B2
APPLICATION NO. : 15/781708
DATED : April 19, 2022
INVENTOR(S) : Simone Carucci et al.

It is certified that error appears in the above-identified patent and that said Letters Patent is hereby corrected as shown below:

In the Claims

Column 4, Line 18 Claim 1 should read as follows:
--A soft gelatin capsule, wherein the capsule comprises a shell containing gelatin, a plasticizer, water and a calcium salt and
a filling,
wherein the filling contains a medicament dispersed or solubilised in a hydrophilic filling comprising from 1 to 5% of gelatin having a Bloom value ranging from 60 to 150 in percentages, from 10 to 30% of hydrolyzed gelatin, from 10 to 30% of 85% glycerol, from 20 to 60% water, from 1 to 5% of pectin, up to 5% of gellan gum and from 0.1 to 10% of alcohol, the percentages being expressed by weight, on the total filling weight, wherein said soft gelatin capsule allows, in vitro, releasing of said medicament in a sustained pH-independent manner, said releasing beginning at the release time of said medicament and continuing for up to 360 minutes.--

Column 4, Line 47 Claim 5 should read as follows:
--A capsule according to claim 1, wherein the shell contains from 20 to 45% of gelatin having a Bloom value ranging from 110 to 300, plasticizer from 15 to 30%, water from 30 to 40% and a calcium salt, the percentages being on the total shell weight.--

Signed and Sealed this
Fifth Day of September, 2023

Katherine Kelly Vidal
*Director of the United States Patent and Trademark Office*